United States Patent [19]
Yang et al.

[11] Patent Number: 5,977,380
[45] Date of Patent: Nov. 2, 1999

[54] PROCESS FOR PREPARING N-[1- (S)-ETHOXYCARBONYL-3- PHENYLPROPYL]-L-ALANINE DERIVATIVES

[75] Inventors: Suh-Wan Yang; Yu-An Chang, both of Tao-yuan Hsien; Yu-Liang Liu, Taipei, all of Taiwan

[73] Assignee: Everlight USA, Inc., Pineville, N.J.

[21] Appl. No.: 09/251,341

[22] Filed: Feb. 17, 1999

[51] Int. Cl.$^6$ .................. C07D 207/12; C07D 233/26; C07D 217/16; C07D 495/10
[52] U.S. Cl. .................. 548/533; 546/133; 546/183; 548/136; 548/322.5; 548/409; 560/39
[58] Field of Search .................. 548/533, 136, 548/322.5, 409; 546/133, 183

[56] References Cited

U.S. PATENT DOCUMENTS

| | | | |
|---|---|---|---|
| 4,716,235 | 12/1987 | Takahashi et al. | 548/533 |
| 5,359,086 | 10/1994 | Merslavic et al. | 548/533 |
| 5,686,627 | 11/1997 | Murthy et al. | 548/533 |
| 5,869,671 | 2/1999 | Wang et al. | 548/533 X |

OTHER PUBLICATIONS

Yamazaki et al., Tetrahedron, 1974, 30(11), 1319–1321.

*Primary Examiner*—Fiona T. Powers
*Attorney, Agent, or Firm*—Bacon & Thomas

[57] ABSTRACT

A process for synthesizing N-[1-(S)-ethoxycarbonyl-3-phenylpropyl]-L-alanine derivatives of the following formula (I):

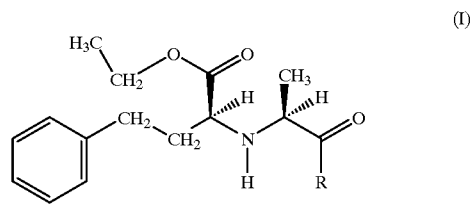

in which the definition of R has the same meaning as given in the description by using a sulfite derivative to activate the C-terminus of the three dimensional structure of an amino acid of N-[1-(S)-ethoxycarbonyl-3- phenylpropyl]-L-alanine, which can effectively couple with another amino acid to form a dipeptide of formula (I). The compound of fomula (I) is an inhibitor of ACE.

8 Claims, No Drawings

PROCESS FOR PREPARING N-[1- (S)-ETHOXYCARBONYL-3- PHENYLPROPYL]-L-ALANINE DERIVATIVES

BACKGROUND OF THE INVENTION

The present invention relates to a process for preparing the derivatives of an inhibitor of Angiotension Converting Enzyme (hereinafter referred to as "ACE"). More particularly, it relates to a process for preparing N-[1-(S)-ethoxycarbonyl-3-phenylpropyl]-L-alanine derivatives.

Life expectancy of a person is prolonged by the breakthrough of medical technology, this contribution yields aged people. Most of the elders suffer from hypertension in some degree. Reducing blood pressure medicine is in mass demand for curing of hypertension. Developing a simple and convenient method to produce a compound that inhibits the ACE activity by means of lowering blood pressure drug thereof is long for decades.

According to U.S. Pat. No. 4,374,829 discloses that by using the derivative of L-alanine-L-proline dipeptide as the reacting agent connects other groups on the N-terminus. During the reaction, a Schiff's base obtained first then undergoes hydrogenation. Meanwhile a mixture of diastereoisomers is RSS and SSS. Among these two isomers, only SSS configuration compound can be used for clinical purpose. Therefore followed by the method mentioned above to separate the SSS configuration from the mixture is the final and critical step as a complete process.

Maintaining the assured stereo chemical structure and avoiding from different one can diminish the difficulties in purification process. In European Patent EP 0215335 discloses that the C-terminus of N-[1-(S)-ethoxycarbonyl-3-phenylpropyl]-L-alanine (hereinafter referred as to NEPA therein reacted with phosgene to form N-[1-(S)-ethoxycarbonyl-3-phenylpropyl]-L-alanine N-carboxyanhydride. Followed by the addition reaction with organic or inorganic slats of L-proline to form derivative of dipeptide. The result yields N-[1-(S)-ethoxycarbonyl-3-phenylpropyl]-L-alanyl-L-proline, a prodrug of ACE inhibitory with SSS configuration of the Enalapilat (common name is Enalapril (2)).

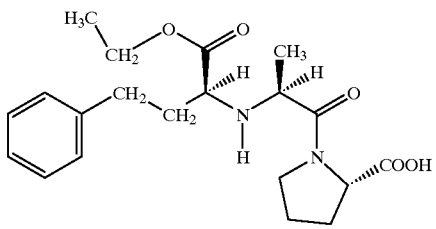

(2)

Although the selectivity of dimensional structure and recovery rate thereof is relatively high during the reaction, it is needed for toxic phosgene in process. As for the purpose of industrial production, there should be a special design for avoiding from the leakage of phosgene, as critical control point for safety control of hazards.

Furthermore, PCT, WO 9602564 discloses that a yield of active thionyldiimidazole by reacting imidazole with thionyl chloride can react with NEPA to form an intermediate of acetyl base; this carboxylate intermediate can again react with amino acid to form an ACE inhibitory compound. In this reaction, using the derivative of sulfite is the derivative of imidazole can cause the second reaction, and moreover the accompanying byproduct will be produced. Therefrom unless purify from the byproduct, this process can not be accounted for a complete process.

SUMMARY OF THE INVENTION

The general object of this invention is to provide a method of simple, convenient, high stereo chemical selectivity, and non-toxic process; to produce a compound with ACE inhibitory activity.

In accordance with the invention, then, a process is provided for synthesizing the ACE inhibitory compound of the following formula (I)

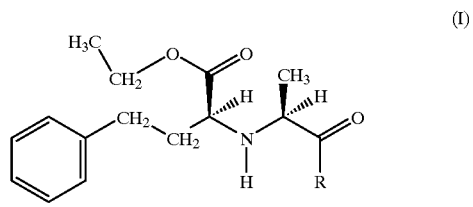

(I)

and its pharmaceutically acceptable salts, wherein R is:

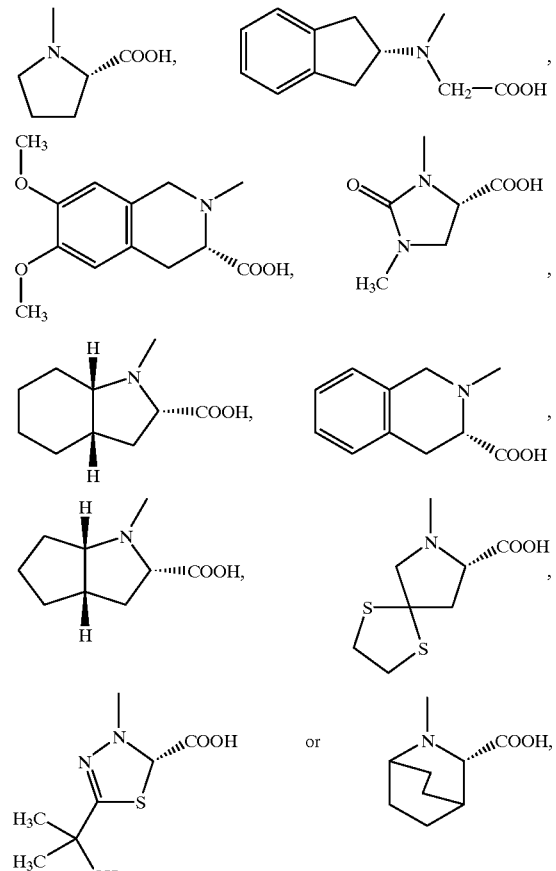

comprises reacting a compound of the following formula (5)

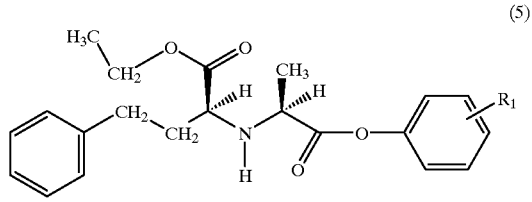
(5)

wherein $R_1$ is nitro, cyano, sulfite, carboxy, aldehyde, ester, or halogen, with amino acid compounds, said amino acid compounds are selected from the group consist of:

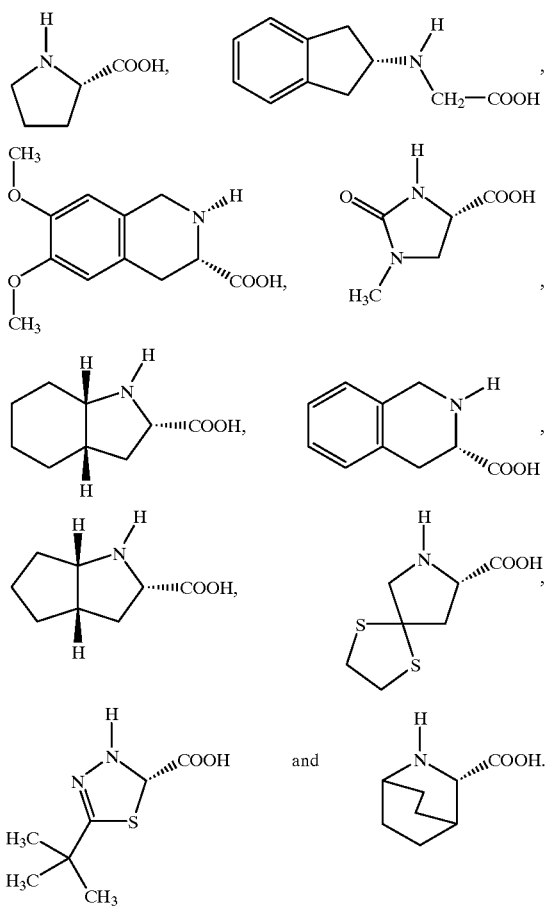

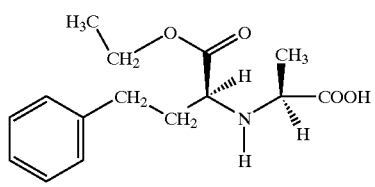
(3)

as a starting material which undergoes reaction with sulfite derivatives of the following formula (4),

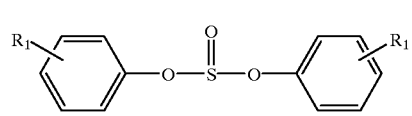
(4)

wherein $R_1$ is nitro, cyano, sulfite, carboxy, aldehyde, ester, or halogen, to get the activated carboxylate intermediate of the following formula (5),

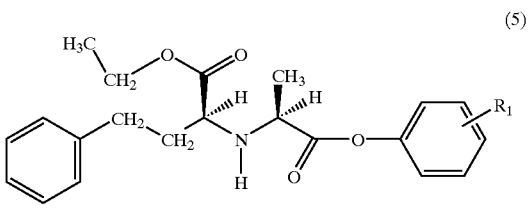
(5)

wherein $R_1$ is defined the same as above.

In this reaction, sulfite derivatives is obtained by reacting phenol derivatives with thionyl chloride in the presence of organic solvent (such as dichloromethane) and triethylamine at a temperature between –20° C. to 25° C. During the above reaction, hydrochloride gas is evolved. Therefore, triethylamine is added into the reaction solution to neutralize hydrochloride.

The activated carboxylate intermediate of formula (5) then can be reacted with the amino acid compounds whish is listed above to form ACE inhibitory compounds.

The most significant character in the present invention is so called one pot reaction. That means the intermediate products will be in situ produced until all reactions have completed and obtained the final products.

More detailed examples are used to illustrate the present invention, and these examples are used to explain the present invention. The examples below, which are given simply by way of illustration, must not be taken to limit the scope of the invention.

DETAILED DESCRIPTION OF THE PREFERRED EMBODIMENTS

The manufacture process of the present invention is using N-[1-(S)-ethoxycarbonyl-3-phenylpropyl]-L-alanine (hereinafter referred as to NEPA) of the following formula (3)

EXAMPLE 1

Synthesis of Sulfite Derivatives

Mix 5000 ml of dichloromethane, 1800 g of 4-nitro phenol, 3650 ml of triethyl amine, and 330 ml of thionyl chloride in a 16L 4-necked round bottle reactor equipped with mechanical stirrer. Stir the mixture for one hour at 0° C., a sulfite derivative of the following formula (6) can be obtained.

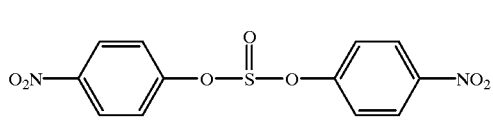

(6)

EXAMPLE 2
Activated Carboxylate Group of NEPA

Add 1000 g of group of NEPA to the above sulfite derivative solution and stir for two hours at 0° C. to get activated carboxylate group of NEPA of the following formula (7)

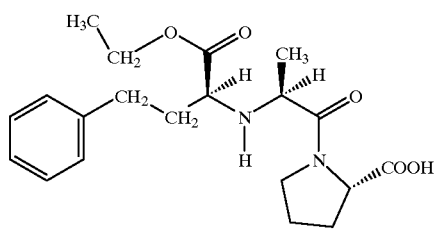

(7)

EXAMPLE 3

Continuously add 450 g L-proline to the above activated carboxylate group of NEPA solution and stir for two hours at 0° C. Add 2000 ml of water then follow by 1200 ml of 32% by weigh of hydrochloric acid. After reaction completed, the SSS configuration of N-[1-(S)-ethoxycarbonyl-3-phenylpropyl]-L-alanyl-proline (common name is Enalapril) of formula (2) is obtained.

(2)

EXAMPLE 4

The organic layer of the above Enalapril solution was condensed, then 8000 ml of ethyl acetate was added into the condensed solution. After added into 370 g of cis-maleic acid, a precipitation of N-[1-(S)-ethoxycarbonyl-3-phenylpropyl]-L-alanine.cis-maleic acid (common name is Enalapril maleate) of the following formula (8) can thus be obtained. The above precipitation was filtered and dryed to get 1117.5 g of Enalapril maleate; mp=144~145° C.

$^1$HNMR (D$_2$O); 1.30(t,3H);1.54,1.59(d,3H);1.80,1.95, 2.00(m,2H);2.02, 2.23,2.25 (m,2H);2.29 (m,2H);2.80 (m,2H);3.45,3.58 (m,2H);3.95,4.41 (t,dd,1H);4.09,4.29 (q,1H );4.26 (q,2H);6.33(s,2H );7.31 (m,3H); 7.39 (t,2H); $^{13}$CNMR; 16.15;(17.43,17.90);(24.93,27.47);(31.80,33.98) ;33.16; (33.90,34.38);(50.30,50.37);(57.88,58.31);(61.49, 61.68); (63.28,63.64);66.90;(129.70,129.75);131.56; 131.80; 136.98; (142.55,142.66);(170.27,170.98);(172.02, 172.17);173.62; (179.17,179.25)

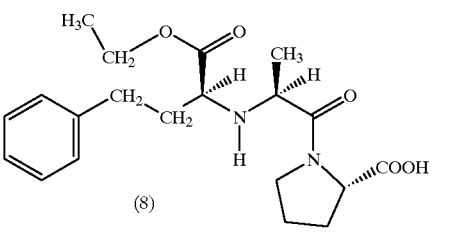

(8)

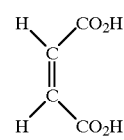

According to the present invention, there is provided a process for preparing ACE inhibitory activity of Enalapril maleate by a convenient, simple, non-toxic and high stereo chemical selectivity. Enalapril maleate is a blood pressure reducing medicine for hypertension.

From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A process for preparing a compound of the following formula (I)

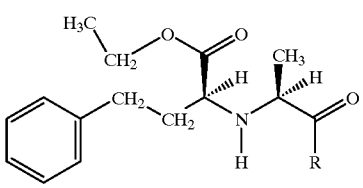

(I)

wherein R is

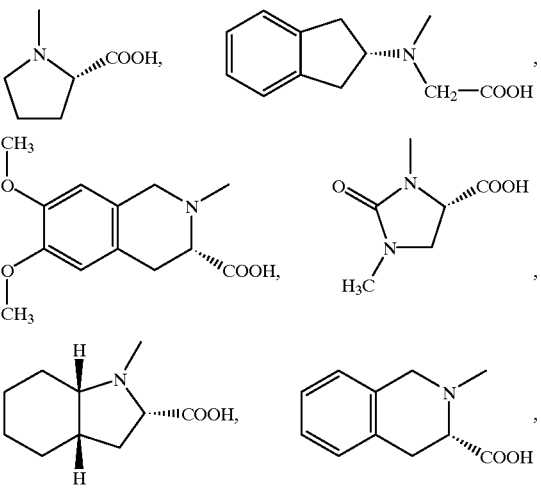

-continued

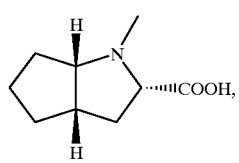 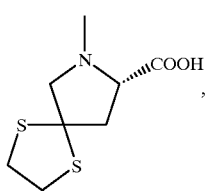

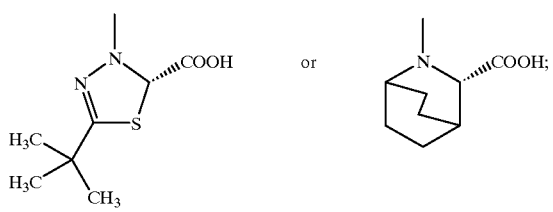

and a pharmaceutically acceptable salt thereof; which comprises reacting the following compound of formula (5)

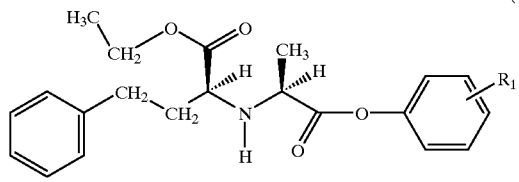

(5)

wherein $R_1$ is nitro, cyano, sulfite, carboxy, aldehyde, ester, or halogen, with a amino acid compound selected from the group consisting of

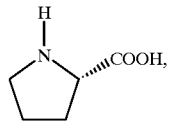 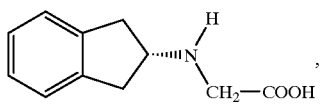

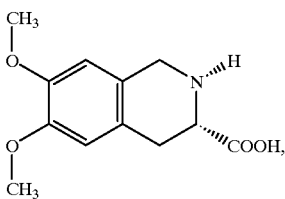 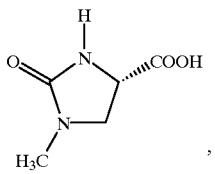

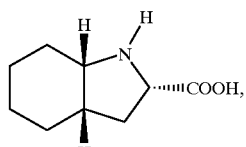 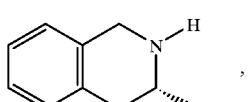

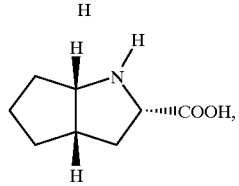 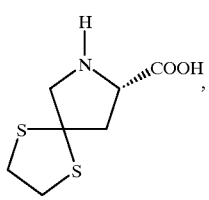

-continued

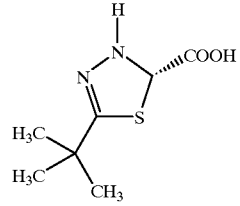 or 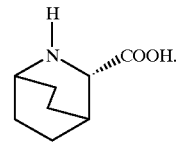

2. The process of claim 1 wherein said compound of formula (5) is synthesized by reacting the following compound (3)

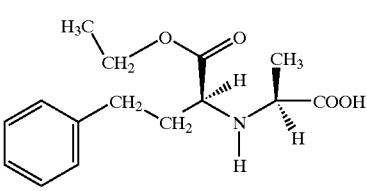

(3)

with a sulfite derivative of the following formula (4)

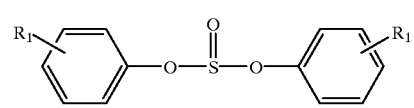

(4)

wherein $R_1$ is nitro, cyano, sulfite, carboxy, aldehyde, ester, or halogen.

3. The process of claim 2 wherein said formula (4) is bis(2-nitrophenyl) sulphite, bis(3-nitrophenyl) sulphite, or bis(4-nitrophenyl) sulphite.

4. The process of claim 1 wherein the amino acid compound is L-proline of the following formula

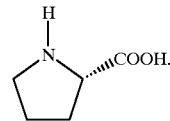

5. The process of claim 2 wherein the amino acid compound is L-proline.

6. The process of claim 1 wherein the compound (I) is a pharmaceutical acceptable salt of hydrochloric acid or sulfuric acid.

7. The process of claim 1 wherein the compound (I) is a compound of the following formula (2)

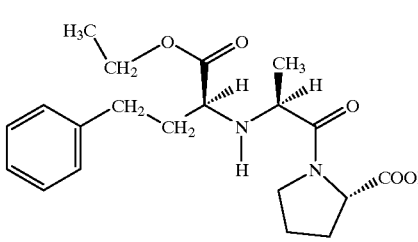

(2)

8. A process for preparing N-[1-(S)-ethoxycarbonyl-3-phenylpropyl]-L-alanyl-L- proline.cis-maleic acid of the following formula (8),

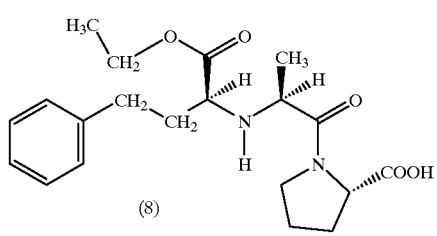
(8)
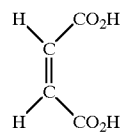
which comprises reacting the formula (2) compound of claim 7 with cis-maleic acid.
* * * * *